United States Patent
Jacobs

(10) Patent No.: US 11,607,447 B2
(45) Date of Patent: Mar. 21, 2023

(54) COMBINATION VACCINE

(71) Applicant: Intervet Inc., Madison, NJ (US)

(72) Inventor: Antonius Arnoldus Christiaan Jacobs, Kessel (NL)

( * ) Notice: Subject to any disclaimer, the term of this patent is extended or adjusted under 35 U.S.C. 154(b) by 58 days.

(21) Appl. No.: 17/270,594

(22) PCT Filed: Aug. 26, 2019

(86) PCT No.: PCT/EP2019/072658
§ 371 (c)(1),
(2) Date: Feb. 23, 2021

(87) PCT Pub. No.: WO2020/043637
PCT Pub. Date: Mar. 5, 2020

(65) Prior Publication Data
US 2021/0252124 A1    Aug. 19, 2021

(30) Foreign Application Priority Data

Aug. 27, 2018    (EP) ..................... 18191018

(51) Int. Cl.
*A61K 39/108* (2006.01)
*A61P 31/04* (2006.01)
*A61K 39/08* (2006.01)
*A61K 39/09* (2006.01)
*A61K 39/00* (2006.01)

(52) U.S. Cl.
CPC .......... *A61K 39/0258* (2013.01); *A61K 39/08* (2013.01); *A61K 39/092* (2013.01); *A61P 31/04* (2018.01); *A61K 2039/54* (2013.01); *A61K 2039/552* (2013.01); *A61K 2039/70* (2013.01)

(58) Field of Classification Search
None
See application file for complete search history.

(56) References Cited

FOREIGN PATENT DOCUMENTS

WO    2008061950 A1    5/2008
WO    2015181356 A1    12/2015

OTHER PUBLICATIONS

European Medicines Agency (CVMP assessment report for Porcilis ColiClos, pp. 1-132, Apr. 11, 2012).*
Baums, C et al, Immunogenicity of an Autogenous *Streptococcus suis* Bacterin in Preparturient Sows and Their Piglets in Relation to Protection after Weaning†, Clinical and Vaccine Immunology, 2010, pp. 1589-1597, vol. 17, No. 10, WO.
Extended European Search report for application 18191018 dated Mar. 19, 2019.
Seele, J et al, The immunoglobulin M-degrading enzyme of *Streptococcus suis*, IdeSsuis, is a highly protective antigen against serotype 2, Vaccine, 2015, pp. 2207-2212, vol. 33 No. 19, Elsevier, EP.
Khishtova N.S., Microbiology of colibacilloses. *Escherichiae coli*, Maikop State Technological University, 2012, 1-2, Lecture No. 4.1.
Khishtova N.S., Microbiology of colibacilloses. *Escherichiae coli*, Maikop State Technological University, 2012, 2, 32, Lecture No. 4 1.—English Translation.
Pan, Zihao et al., Novel Variant Serotype of *Streptococcus suis* Isolated from Piglets with Meningitis, Applied and Environmental Microbiology, 2015, 976-985, 81(3).
Porcilis ColiClos *E. Coli* and *C. perfringens* vaccine, CTP.1-3, https://www.ema.europa.eu/en/medicines/veterinary/EPAR/porcilis-coliclo, 3 pages, 2012.
Dewilde, Combination Vaccines: How and Why? Lessons Learned, Global Vaccine and Immunization Research Forum Johannesburg, 2016, pp. 1-23; Retrieved from World Health Organization, https://www.who.int/immunization/research/forums_and_initiatives/1_MWilde_Combination_Vaccines_gvirf16.pdf?ua=1.

* cited by examiner

*Primary Examiner* — Brian Gangle
(74) *Attorney, Agent, or Firm* — Michael D. Davis

(57) ABSTRACT

The present invention pertains to a vaccine comprising (a) an immunologically effective amount of a *Streptococcus suis* IgM protease antigen, (b) an immunologically effective amount of an *Escherichia coli* fibmrial antigen, and (c) an immunologically effective amount of a *Clostridium* toxoid, and also pertains to use of the vaccine in a method for protecting pigs against a pathogenic infection with *Streptococcus suis*, *Escherichia coli* and *Clostridium*.

14 Claims, No Drawings

COMBINATION VACCINE

CROSS-REFERENCE TO RELATED APPLICATIONS

This application is a national stage entry under 35 U.S.C. § 371 of PCT/EP2019/072658, filed Aug. 26, 2019, which claims priority to EP Application No. EP18191018.3, filed Aug. 27, 2018. The content of PCT/EP2019/072658 is hereby incorporated by reference in its entirety.

GENERAL FIELD OF THE INVENTION

The invention pertains to a combination vaccine for protection of pigs against a pathogenic infection with *Streptococcus suis, Escherichia coli* and *Clostridium*.

BACKGROUND OF THE INVENTION

The present invention relates to the field of veterinary vaccinology, namely to combination vaccines for swine. In particular the invention relates to a combination vaccine comprising antigens from *Streptococcus suis* (*S. suis*), *Escherichia coli* (*E. coli*) and *Clostridium*.

Intensive swine farming today, relies heavily on veterinary medical products to keep animals healthy, and allow an economic operation. Next to optimisation of the feed and of farm management systems, a variety of treatments are regularly used: pharmaceuticals such as hormones or antibiotics, and vaccination against bacterial- or viral pathogens.

Currently used vaccines for protection against bacterial pathogens are mainly whole-cell bacterins. However, field reports describe difficulty in disease control and management, and specially "vaccine failures" are common. Carrier pigs are the primary source of infection, and both vertical and horizontal transmission are involved in spread of the disease within a herd. Mixing of carrier animals with susceptible animals under stressful conditions such as weaning and transportation usually results in clinical disease. Therefore, effective control measures to prevent disease will hinge on prophylactic/metaphylactic procedures (where allowed) and on vaccination. Currently, field immunization efforts have focused on the use of commercial or autogenous bacterins. These vaccine strategies have been applied to either piglets or sows. Sow vaccination is less costly and labor intensive, thus representing an economical alternative to piglet vaccination. Yet, available results seem to indicate that sow vaccination with bacterins is also a matter of controversy. In many cases vaccinated sows, even when vaccinated twice before parturition, respond poorly or not at all to vaccination which results in low maternal immunity transferred to the litters. And even if maternal immunity is transferred at a sufficient level, in many cases the maternal antibodies are too low to provide protection in the most critical period of 4-7 weeks of age. Sow vaccination is conventionally used for protection against a variety of pathogenic infections, such as infections caused by *E. coli, Clostridium, Pasteurella multocida, Bordetella bronchiseptica*, porcine circovirus, and the like. *Streptococcus suis* is a commensal and opportunistic pathogen of swine. In particular under stress, the bacterium may elicit a pathogenic infection and induce disease. Early medicated weaning and segregated early weaning practices do not eliminate *Streptococcus suis* infection. From weaning and onwards piglets are more susceptible to *Streptococcus suis* infections due to the stresses associated with weaning and also, the common subsequent transport. Therefore, prepartum immunization in sows is often used to try and convey passive immunity to piglets and provide protection against *Streptococcus suis* under these stressful circumstances early in life.

Under modern pig producing conditions, major stress is induced for example by weaning of piglets and transport of young piglets. This has made *Streptococcus suis* to become a major swine pathogen. It is also an emerging zoonotic agent of human meningitis and streptococcal toxic shock-like syndrome. *Streptococcus suis* is a well-encapsulated pathogen and multiple serotypes have been described based on the capsular polysaccharide antigenic diversity. *Streptococcus suis* uses an arsenal of virulence factors to evade the host immune system. Together, these characteristics have challenged the development of efficacious vaccines to fight this important pathogen. Recently, an overview article has been published regarding vaccines against *Streptococcus suis* (Mariela Segura: "*Streptococcus suis* vaccines: candidate antigens and progress, in *Expert Review of Vaccines*, Volume 14, 2015, Issue 12, pages 1587-1608). In this review, clinical field information and experimental data have been compiled and compared to give an overview of the current status of vaccine development against *Streptococcus suis* as outlined here below.

In pigs, autogenous bacterins are frequently used in the field for protection against *Streptococcus suis*, especially in Europe. They are prepared from the virulent strain isolated on the farm with clinical problems and applied to the same farm. One of the disadvantages of autogenous bacterins is that vaccine safety data are lacking and severe adverse reactions may occur. Sampling errors (due to using only one or two pigs or samples) may result in failure to identify a strain or serotype associated with a recent outbreak. This failure may be especially problematic in endemic herds. Finally, the most important dilemma of autogenous bacterins is that their actual efficacy has been poorly studied. As application of autogenous vaccines is empirical, it is not surprising that results obtained with these vaccines are inconsistent.

Other experimental vaccines are also described in the art. Kai-Jen Hsueh et al. show ("Immunization with *Streptococcus suis* bacterin plus recombinant Sao protein in sows conveys passive immunity to their piglets", in: *BMC Veterinary Research, BMC series—open, inclusive and trusted*, 13:15, 7 Jan. 2017) that a bacterin plus subunit might be a basis for successful vaccination of sows to confer protective immunity to their piglets.

Live attenuated vaccines have also been contemplated in the art. Non-encapsulated isogenic mutants of *Streptococcus suis* serotype 2 have been clearly shown to be avirulent. Yet, a live vaccine formulation based on a non-encapsulated serotype 2 mutant induced only partial protection against mortality and failed to prevent the development of clinical signs in pigs challenged with the wildtype strain (Wisselink H J, Stockhofe-Zurwieden N, Hilgers L A, et al. "Assessment of protective efficacy of live and killed vaccines based on a non-encapsulated mutant of *Streptococcus suis* serotype 2." in: *Vet Microbiol*. 2002, 84:155-168.)

In the last couple of years, an extensive list of antigenic or immunogenic *Streptococcus suis* molecules has been reported, and most of these have been discovered through immuno proteomics using either convalescent sera from infected pigs or humans and/or laboratory-produced immune sera. WO2015/181356 (IDT Biologika GmbH) has shown that IgM protease antigens (either the whole protein or the highly conserved Mac-1 domain representing only about 35% of the full protein) can elicit a protective immune response in piglets in a vaccination scheme of administering two doses of the IgM protease antigen, optionally in combination with a prime vaccination containing a bacterin. It is noted that WO2017/005913 (Intervacc AB) also describes the use of an IgM protease antigen (in particular, an IgM protease polypeptide fused to a nucleotidase) but only the property of being able to elicit a seroresponse has been shown. A protective effect for an IgM protease antigen is not shown in this international patent application.

*Escherichia coli* is a gram negative peritrichously flagellated bacteria belonging to the family Enterobatteriaceae and is the causative agent of a wide range of diseases in pigs, which are important causes of death occurring worldwide in suckling and weaned pigs respectively. *E. coli* infection, or colibacillosis, affects both indoor and outdoor herds, occurring both chronically and sporadically. *E. coli* infections occur at three main stages: neonatal diarrhea (in the first few days after farrowing), young piglet diarrhea (from the first week post-farrowing to weaning) and post-weaning diarrhea (in the first weeks after weaning). They can also be present in combination with other pathogens including rotavirus, and cause other diseases such as edema disease and urinary tract infections.

Certain strains of *E. coli* possess fimbria or pili that allow them to adhere to or colonize the absorptive epithelial cells of the jejunum and ileum. The common antigenic types of pili associated with pathogenicity are F4 (=K88), F5 (=K99), F6 (987P), and F41. Pathogenic strains produce enterotoxins that cause fluid and electrolytes to be secreted into the intestinal lumen, which results in diarrhea, dehydration, and acidosis. Infection in neonates is commonly caused by K88 and 987P strains, whereas postweaning colibacillosis is nearly always due to the K88 strain. See Vet Rec. 2002 Jan. 12; 150(2): 35-7.

Various approaches have been used to prevent colibacillosis, in particular post-weaning diarrhea, including passive administration with specific antibodies, dietary supplementation such as prebiotics and probiotics and dietary preventive measures, genetic breeding for ETEC-resistant herds and live oral nontoxigenic *E. coli* vaccine (Luppi A., Swine enteric colibacillosis: diagnosis, therapy and antimicrobial resistance, Porcine Health Manag. 2017; 3: 16; Zhang W. Progress and Challenges in Vaccine development against enterotoxigenic *Escherichia coli* (ETEC)—Associated porcine Post-weaning Diarrhea (PWD) J Vet Med Res. 2014; 1(2):1006). Commercial vaccines are available, e.g. Porcilis® ColiClos (MSD Animal Health), Gletvax® and Litterguard® (both of Zoetis), Clostricol® (IDT Biologika), Entericolix® (Boehringer Ingelheim). Piglets can be adequately protected against *E. coli* through the intake of colostrum of vaccinated mother animals.

*Clostridium*, an anaerobic, gram-positive, sporeforming rod, is an important emerging pathogen that causes diarrhea primarily in neonatal swine. The agent was first recognized as a cause of antibiotic-associated diarrhea in people. It most commonly causes disease in piglets 1-7 days old and in other domestic and laboratory animals. *Clostridium* infection includes infections by *C. difficile* and *C. perfringens*. The organism can be demonstrated in the intestine by direct Gram stain of smears. Survival of *Clostridium* in the environment and shedding by carrier sows is believed to be important in transmission. *Clostridium perfringens* type C and to a lesser extent type B, are important pathogens of swine. It is known that the corresponding toxoids are able to induce a protective immune response in swine. Various commercial vaccines are available, Porcilis® ColiClos (MSD Animal Health), Gletvax® and Litterguard® (both of Zoetis), Clostricol® (IDT Biologika), Entericolix® (Boehringer Ingelheim). Piglets can be adequately protected against *Clostridium* through the intake of colostrum of vaccinated mother animals.

To limit stress to the animals and cost and labor for the caretakers, it is generally desired to provide protection against more than one disease. Thus, there is a need to provide a swine vaccine for protection against *Streptococcus suis* in addition to protection against other swine diseases. However, the efficacy of a combination vaccine is unpredictable beforehand due to possible incompatibilities of vaccine components, such as negative interference between the antigens or other vaccine components, which could lead to reduced vaccination efficacy or enhanced adverse effects. Although the combination of antigens in one vaccine as such has been, and still is, a common desire, for any combination vaccine in particular the problem of interference between antigens is a very common problem which prevents many if not most combinations of antigens to be developed in multivalent vaccines. For this we refer to a lecture of Michel De Wilde of March 2016, title "*Combination vaccines: how and why? Lessons learned*", which is accessible via the website of the World Health Organization. The lecture confirms that there is common desire to strive for combination vaccines, but also that amongst other problems, there are many scientific and technical problems to overcome. Examples of failed developments of combination vaccines using common antigens are shown.

OBJECT OF THE INVENTION

It is thus an object of the present invention to find a combination vaccine to protect a pig, in particular a piglet, against a pathogenic infection including *Streptococcus suis*. In addition, it is an object of the invention to find a combination vaccine to protect a piglet against more than one pathogenic infection, wherein protection of the piglet against these infections is achieved by sow vaccination.

SUMMARY OF THE INVENTION

It has surprisingly been found in the present invention that a combination vaccine can be provided for protection of pigs against a pathogenic infection with *Streptococcus suis, Escherichia coli* and *Clostridium*. Further, it has surprisingly been found that the vaccine can be administered to a female pig in order to protect a piglet against a pathogenic infection with *Streptococcus suis, Escherichia coli* and *Clostridium* through the intake of colostrum of the vaccinated female pig.

In order to meet the object of the invention a vaccine according to claim 1 is provided comprising components (a), (b) and (c) of:
  (a) an immunologically effective amount of a *Streptococcus suis* IgM protease antigen,
  (b) an immunologically effective amount of an *Escherichia coli* fimbrial antigen, and
  (c) an immunologically effective amount of a *Clostridium* toxoid.

Preferred embodiments of the present invention are defined in the dependent claims.

Thus, the present invention for the first time provides a combination vaccine (short: vaccine according to the present invention) which provides protection against multiple pathogenic infections including an infection caused by *S. suis*. Further, it has become possible with the present invention to protect a piglet against multiple pathogenic infections, including an infection caused by *S. suis*, through sow vaccination.

The invention is thus also provides a kit of parts comprising multiple separate vaccine containers, one of which comprises an immunologically effective amount of a *Streptococcus suis* IgM protease antigen, and one or more additional containers in combination comprise an immunologically effective amount of an *Escherichia coli* fimbrial antigen, and an immunologically effective amount of a *Clostridium* toxoid (for example one container comprising both *E. coli* and Clostridial antigens, or two or more separate containers each comprising on or more of the respective antigens).

The invention also provides a vaccine comprising an immunologically effective amount of a *Streptococcus suis* IgM protease antigen, for use in a method to protect an animal against *Streptococcus suis* infection, *Escherichia coli* infection and *Clostridium* infection, wherein the IgM protease antigen is mixed with an immunologically effective amount of an *Escherichia coli* fimbrial antigen, and an immunologically effective amount of a *Clostridium* toxoid, before administration of the vaccine.

DEFINITIONS

A vaccine is a pharmaceutical composition that is safe to administer to a subject animal, and is able to induce protective immunity in that animal against a pathogenic micro-organism, i.e. to induce a successful protection against the micro-organism.

A *Streptococcus suis* IgM protease antigen is an enzyme that specifically degrades porcine IgM (and not porcine IgG or porcine IgA; Seele et al, in *Journal of Bacteriology*, 2013, 195 930-940; and in *Vaccine* 33:2207-2212; 5 May 2015), a protein denoted as Ide$_{Ssuis}$, or an immunogenic part thereof (typically having a length of at least about 30-35% of the full-length enzyme). The whole enzyme has a weight of about 100-125 kDa, corresponding to about 1000-1150 amino acids, the size depending on the serotype of *S. suis*. In WO 2015/181356 several sequences that represent an IgM protease antigen of *Streptococcus suis* are given, viz. SEQ ID NO:1, SEQ ID NO:2, SEQ ID NO:6, SEQ ID NO:7 and SEQ ID NO:5, the latter being an immunogenic part of the full-length enzyme (denoted as the Mac-1 domain, i.e. amino acids 80-414 of SEQ ID NO:7). Other examples of immunogenic parts of the full-length enzyme are given in WO2017/005913. In particular the IgM protease may be the protease according to SEQ ID NO:1 of WO2015/1818356 or a protein having at least 90%, or even 91, 92, 93, 94, 95, 96, 97, 98, 99% up to 100% sequence identity in the overlapping regions. The amino acid sequence identity may be established with the BLAST program using the blastp algorithm with default parameters. It is expected that the IgM protease of *Streptococcus suis* of various serotypes have a sequence identity higher than 90%, in particular expected to be 91, 92, 93, 94, 95, 96, 97, 98, 99% up to 100%. An artificial protein, for example made to optimize yield in a recombinant production system of the antigen, may lead to a lower amino acid sequence identity such as 85%, 80%, 75%, 70% or even 60% compared with the whole enzyme, while maintaining the required immunogenic function, and is understood to be an IgM protease antigen of *Streptococcus suis* in the sense of the present invention.

Protection against a micro-organism is aiding in preventing, ameliorating or curing a pathogenic infection with that micro-organism or a disorder arising from that infection, for example to prevent or reduce one or more clinical signs resulting from the infection with the pathogen.

An "immunologically effective amount" as used herein relates to the amount of antigen or toxoid that is necessary to induce an immune response in pigs to the extent that it decreases an infection with or the pathological effects caused by the infection with a wild-type infectious agent, i.e. *S. suis*, *E. coli* or *Clostridium*, when compared to the pathological effects caused by infection with a wild-type infectious agent in non-immunized pigs. The immunologically effective amount can be established by the skilled person via routine methods commonly known in the art, for instance by administering an experimental challenge infection to vaccinated animals and next determining a target animal's clinical signs of disease, serological parameters or by measuring re-isolation of the pathogen, followed by comparison of these findings with those observed in field-infected pigs.

DESCRIPTION OF EMBODIMENTS

Component (a) of the vaccine according to the invention comprises an immunologically effective amount of *Streptococcus suis* IgM protease antigen in order to provide protection against an infection by *S. suis*.

Component (a) thus is conventionally included for conferring protection against clinical signs associated with a pathogenic infection with *Streptococcus suis*. Typical clinical signs associated with a pathogenic infection with *Streptococcus suis* are increased rectal temperature, impaired locomotion (limping, swollen joints), increased respiration rate and neurological signs (e.g. tremors, convulsions, torticollosis, ataxia). Preventing, amelioration or curing one or more of these signs will be beneficial for the pig, not only since it is an indication that the pathogenic infection is being suppressed. In yet another embodiment the vaccine is for conferring protection against an increased mortality associated with a pathogenic infection with *Streptococcus suis*.

The vaccine according to the present invention typically comprises the IgM protease antigen in an amount below 250 μg per dosis of the vaccine, preferably at 120 μg per dosis or below. The minimum amount is the amount at which protective immunity can still be obtained. This can be established by routine experimentation and depends i. a. on the immunogenic properties of the IgM protease antigen chosen but also on the required level of protection. For the current vaccine, a minimum amount is believed to be 1 μg of the antigen per dosis, but it may be any higher dosis such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or any higher integer in the range 61-119 up to and including 120 μg per dosis.

Component (b) of the vaccine according to the invention comprises an immunologically effective amount of an *E. coli* fimbrial antigen and optionally a toxoid in order to provide protection against an infection by *E. coli*. Component (b) thus is conventionally included for conferring protection against clinical signs associated with a pathogenic infection with *E. coli* including profuse watery diarrhea with rapid dehydration, acidosis, and death is common. Rarely, pigs may collapse and die before diarrhea begins.

Pathogenic infection by *E. coli* typically comprises, without being limited thereto, infection caused by enterotoxigenic *E. coli* as well as infection caused by enteropathogenic *E. coli* strains.

*E. coli* can be categorized based on elements that can elicit an immune response in animals, i.e. *E. coli* antigens. These antigens can be used for vaccination singly or in combination in order to provide protection against *E. coli* infection. *E. coli* antigens comprise the O antigens forming part of the lipopolysaccharide layer, the K antigen forming the capsule, the H antigens forming flagellin, and the fimbrial F antigens. Component (b) of the vaccine according to the invention at least comprises one or more F antigens.

In addition, one or more of *E. coli* toxins, such as enterotoxins, may be used as toxoids in a vaccine according to the invention. *E. coli* enterotoxins include, but are not limited to, ST enterotoxin and LT enterotoxin. The most important antigens and enterotoxins causing enteric colibacillosis are, for example, described in Luppi A., Swine enteric colibacillosis: diagnosis, therapy and antimicrobial resistance, Porcine Health Manag. 2017; 3: 16; Zhang W. Progress and Challenges in Vaccine development against enterotoxigenic *Escherichia coli* (ETEC)—Associated porcine Post-weaning Diarrhea (PWD) J Vet Med Res. 2014; 1(2):1006.

Typically, the vaccine according to the invention comprises one or more *E. coli* F antigens and optionally *E. coli* LT toxoid. In a preferred embodiment, the vaccine comprises one or more antigens selected from fimbrial proteins F4, including F4ab(=K88ab) and F4ac(=K88ac), F5(=K99), F6(=987P), F18, F41 and optionally *Escherichia coli* LT toxoid. More preferably, it comprises at least the fimbrial *E. coli* antigens F4, including F4ab(=K88ab) and F4ac (=K88ac), F5 and F6. In another preferred embodiment, the vaccine comprises the fimbrial antigens F4, including F4ab (=K88ab) and F4ac(=K88ac), F5, F6, and optionally *E. coli* LT toxoid.

Component (c) of the vaccine according to the invention comprises an immunologically effective amount of *Clostridium* toxoid in order to provide protection against an infection by *Clostridium*. Component (c) thus is conventionally included for conferring protection against clinical signs associated with a pathogenic infection with *Clostridium* including diarrhea, dyspnea, abdominal distention, and scrotal edema.

Preferably, component (c) comprises one or more *Clostridium* toxoids selected from *Clostridium* toxoid B and *Clostridium* toxoid C. More preferably, component (c) comprises one or more toxoids selected from *Clostridium perfringens* type B toxoid (perfB), *Clostridium perfringens* type C toxoid (perfC) and *Clostridium novyi* type B toxoid (novyiB), and most preferably the *Clostridium perfringens* type C toxoid (perfC). In a most preferred embodiment, component (c) comprises *Clostridium perfringens* type C toxoid, and may optionally further comprise *Clostridium perfringens* type B toxoid.

In a particularly preferred embodiment according to the invention, component (b) comprises at least the *E. coli* fimbrial antigens F4, F5, and F6 and component (c) comprises the *Clostridium perfringens* type C toxoid.

In a further preferred embodiment, the immunologically effective component of the vaccine according to the invention consists of the *Streptococcus suis* IgM protease antigen, the *E. coli* antigens F4, F5 and F6 and optionally LT toxoid, and the *Clostridium perfringens* type C toxoid.

In a vaccine according to the invention, the antigen is typically combined with a pharmaceutically acceptable carrier, i.e. a biocompatible medium, i.e. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the vaccine.

The vaccine according to the present invention typically comprises an adjuvant. Conventional adjuvants, well-known in the art are e.g. Freund's Complete and Incomplete adjuvant, tocopherol-alpha, vitamin E, non-ionic block polymers, muramyl dipeptides, Quill A®, mineral oil, e.g. Bayol® or Markol®, vegetable oil, and Carbopol® (a homopolymer), or Diluvac® Forte.

The vaccine may also comprise a so-called "vehicle". A vehicle is a compound to which the polypeptide adheres, without being covalently bound to it. Often used vehicle compounds are e.g. aluminum hydroxide, -phosphate or -oxide, silica, Kaolin, and Bentonite.

The vaccine according to the present invention may be administered by any suitable route of administration, including parenteral administration, e.g. through all routes of injection into or through the skin, e.g. intramuscular, intravenous, intraperitoneal, intradermal, submucosal, or subcutaneous, but is typically adapted, i.e. suitable, for intramuscular injection.

In another embodiment, the present invention relates to a vaccine as described herein for use in a method for protecting pigs against a pathogenic infection with *Streptococcus suis, Escherichia coli* and *Clostridium*.

In another embodiment, the present invention relates to the use of a vaccine as described herein for the manufacture of a medicament for use in protecting pigs against a pathogenic infection with *Streptococcus suis, Escherichia coli* and *Clostridium*.

The vaccine of the present invention is in particular used for the passive immunization of progeny by active immunization of sows and gilts to reduce mortality and/or clinical signs of pathogenic infections caused by *S. suis*, caused by those *E. coli* strains, which express in particular the adhesins F4ab (K88ab), F4ac (K88ac), F5 (K99) and/or F6 (987P), and caused by *C. perfringens* type C.

A commercially available vaccine for providing protection against such infections caused by *E. coli* and *Clostridium* is Porcilis ColiClos® available from MSD Animal Health, including the *E. coli* components F4ab fimbrial, F4ac fimbrial adhesin, F5 fimbrial adhesin, F6 fimbrial adhesin, LT toxoid; and the *Clostridium perfringens* component Type C (strain 578) beta. Thus, in another preferred embodiment, the vaccine according to the invention may be prepared by mixing the commercially available vaccine Porcilis ColiClos® with a suitable amount of the *S. suis* IgM antigen.

Surprisingly, it has been found that by using an IgM protease antigen (thus even when using a vaccine that comprises as porcine antigen only the IgM protease antigen of *Streptococcus suis*), to induce antibodies in a female animal, piglets arrive at adequate protection against *Streptococcus suis* through the intake of colostrum of the vaccinated animal. Therefore, an antigen that was shown to have a protective effect in piglets, has been shown to be useful for vaccinating sows to arrive at a clear protective effect in piglets, typically at least in the window of 2-3 weeks after weaning.

The invention thus also pertains to the use of an IgM protease antigen of *Streptococcus suis* for the manufacture of a combination vaccine for protecting a piglet against *Streptococcus suis, E. coli* and *Clostridium* by administering the combination vaccine to a female pig and allowing the piglet to take up colostrum form the vaccinated female pig. As indicated here above, to arrive at optimum protection, the colostrum is typically taken up within 48 hours, in particular within 24 hours after birth of the piglet.

In another preferred embodiment, the vaccine according to the invention is administered to a female pig in order to protect a piglet against a pathogenic infection with *Streptococcus suis*, *Escherichia coli* and *Clostridium* through the intake of colostrum of the vaccinated female pig.

Further, the present invention is described by way of the following non-limiting examples.

EXAMPLES

Example 1

Objective

The objective of this study was to test the efficacy of an IgM protease subunit vaccine in pregnant sows against *Streptococcus suis* challenge of the offspring at different ages, viz. at 4, 6, 8 and 10 weeks of age.

Study Design

For this study, 12 pregnant gilts were used. Six gilts were vaccinated at 6 and 2 weeks before estimated parturition with a recombinant rIde$_{Ssuis}$ IgM protease antigen (Seele et al: Vaccine 33:2207-2212; 5 May 2015, par. 2.2.) at 120 µg per dose (as established by a Bradford protein assay using BSA as a standard) in XSolve adjuvant (MSD Animal Health, Boxmeer, The Netherlands). Six gilts were left as unvaccinated controls. After delivery the piglets of the sows were divided into four challenge groups of 20 piglets each (10 piglets from vaccinated sows and 10 piglets from control sows), providing an even distribution of the different litters over the groups. The four groups were challenged at 4, 6, 8 and 10 weeks of age, respectively with a virulent culture of *S. suis* serotype 2. During 9-11 days after challenge the piglets were daily observed for clinical signs of *S. suis* infection such as depression, locomotory problems and/or neurological signs using a regular scoring system going from 0 (no signs) to 3 for severe cases. The same scoring system (0 for parameter not visible, the highest number for severe cases) was used for each parameter. Animals reaching the humane endpoint were euthanized. At regular times before and after vaccination (sows) and just before challenge (piglets) serum blood was collected for antibody determination. At regular times before and after challenge heparin blood was collected from the piglets for re-isolation of challenge strain. Thirteen weeks after booster vaccination, 4 sows were necropsied and the injection site was examined for local reactions or vaccine remnants.

Results

Four vaccinated sows were subjected to a post-mortem examination of the injection site. Two animals had a small (2-3 cm diameter) local reaction at the booster injection site consisting of a discoloration with increased tissue consistency. No abscesses or vaccine remnants were observed. It could therefore be concluded that the vaccine was safe to administer.

On day of first vaccination (6 weeks before estimated delivery) the gilts had (low) IgG antibody titres against the antigen. After vaccination, the vaccinated gilts showed a clear seroconversion whereas the control animals remained at a low level. Average IgG titres in colostrum were 8.8 log$_2$ higher in vaccinated animals as compared to the controls. After suckling, the piglets of the vaccinated dams had approximately 7.7 log$_2$ higher serum titres compared to control animals. The difference in average titre at 4, 6, 8 and 10 weeks of age were 6.7, 5.3, 4.8 and 3.6 log$_2$, respectively. The post challenge data for the period before euthanisation (days 9-11) are indicated in Table 1.

TABLE 1

| | Results post-challenge | | | |
|---|---|---|---|---|
| Age | Group | Clinical score (av) | # euth. per total | Survival time (av-davs) |
| 4 weeks | Vaccine | 17.1 | 3/10 | 9.5 |
| | Control | 31.6 | 6/10 | 8.0 |
| 6 weeks | Vaccine | 5.8$^a$ | 2/10$^b$ | 8.8$^a$ |
| | Control | 59.7 | 9/10 | 2.7 |
| 8 weeks | Vaccine | 2.3$^a$ | 0/10$^b$ | 11.0$^a$ |
| | Control | 59.5 | 8/10 | 4.7 |
| 10 weeks | Vaccine | 0.7$^a$ | 0/10 | 10.0 |
| | Control | 15.6 | 2/10 | 8.8 |

$^a$significantly different from control group (Mann Whitney U test, $p < 0.05$)
$^b$significantly different from control group (Fisher's exact test, $p < 0.05$)

Conclusion

From the results it can be concluded that sow vaccination with the IgM protease subunit vaccine is an adequate vaccination strategy to control *Streptococcus suis* infections in piglets. The vaccine induced markedly better protection against *Streptococcus suis* challenge up to 10 weeks of age when compared with the protection arrived at in piglets receiving colostrum from naturally infected mother animals. This shows that the piglets can be protected in the complete period of 2-3 weeks after weaning, i.e. within the period when the piglets have an age of 4-7 weeks, and even beyond that period.

Example 2

Objective

The aim of this study was to test the serological response of different combination vaccines including the recombinant *S. suis* IgM antigen rIde$_{Ssuis}$ compared to the single vaccines. In particular the combination with a combined *E. coli*/*Clostridium* vaccine (comprising fimbrial *E. coli* antigens and *Clostridium perfringens* Type C toxoid), as well as with a combined *Pasteurella/Bordetella* vaccine (comprising *Pasteurella* toxin and inactivated *Bordetalla* cells) was assessed. Specifically, the serological response was tested after associated mixed use of a rIde$_{Ssuis}$ subunit vaccine with the commercial vaccines Porcilis® ColiClos or Porcilis® AR-T DF compared to the single vaccines.

Study Design

For this study 48 healthy 17-week-old pigs were used, allotted to six groups of 8 animals each. Group 1 was vaccinated with the subunit antigen in Diluvac® Forte adjuvant, group 2 was vaccinated with the subunit antigen in Porcilis® ColiClos, group 3 was vaccinated with the subunit antigen in Porcilis® AR-T DF, and groups 4 and 5 were vaccinated with either Porcilis® ColiClos or Porcilis® AR-T DF, respectively. Vaccinations were administered intramuscularly in the neck at 17 weeks of age and 21 weeks of age. At 23 weeks of age all animals were post-mortem examined for local reactions at the injection sites. Blood samples were collected just before each vaccination and during euthanasia at post-mortem.

Materials and Methods

Concentrated rIde$_{Ssuis}$ Subunit Antigen

Product name: Subunit antigen (rIde$_{Ssuis}$)

Pharmaceutical form: Suspension containing 0.64 mg/ml antigen

Presentation: 1.50 ml fill (1.8 ml cryotubes)
Diluvac® Forte Adjuvant
Product name: Diluvac® Forte
Pharmaceutical form: Emulsion for intramuscular application
Presentation: 20 ml fill (20 ml PET vial)
Vaccine Porcilis® ColiClos
Product name: Porcilis® ColiClos
Pharmaceutical form: Emulsion for intramuscular application
Presentation: 20 ml fill (20 ml PET vial)
Vaccine Porcilis® AR-T DF
Product name: Porcilis® AR-T DF
Pharmaceutical form: Emulsion for intramuscular application
Presentation: 20 ml fill (20 ml PET vial)

rIde$_{Ssuis}$ Vaccines rIde$_{Ssuis}$ vaccines in Diluvac Forte, Porcilis ColiClos and Porcilis AR-T DF were prepared just before use by adding 1.3 ml purified rIde$_{Ssuis}$ (concentration 0.64 mg/ml) to one vial (20 ml) of either Diluvac Forte, Porcilis ColiClos or Porcilis AR-T DF, resulting in a vaccine containing 40 μg/ml=80 μg per dose. The vaccine was transported at 2-8° C.

Test System

Animals, Identification, Housing and Husbandry

Forty-eight pigs, identified by numbered ear tags were used. At day of first vaccination the pigs were 17 weeks of age. One week before first treatment the pigs were housed. During the experiment the pigs were fed according to standard procedures and had access to fresh tap water ad libitum. The acclimatization was one week. Only healthy animals were included in the experiment. Pigs were assigned to the 5 treatment groups and vaccinated as they came to hand.

Treatment

The pigs were vaccinated as described below.

| group | #pigs | vaccine | vaccination volume/ route/age | bloodsampling |
|---|---|---|---|---|
| 1 | 8 | $rIde_{Ssuis}$ + Diluvac Forte | 2 mL/IM/ 17w and 21w | 17w, 21w, 23w |
| 2 | 8 | $rIde_{Ssuis}$ + Porcilis ColiClos | | |
| 3 | 8 | $rIde_{Ssuis}$ + Porcilis AR-T DF | | |
| 4 | 8 | Porcilis ColiClos | | |
| 5 | 8 | Porcilis AR-T DF | | |

Therefore, group 2 represents a combination vaccine according to the invention whereas groups 1 and 3 to 5 represent comparative vaccines (control groups).

Animal Experimental Procedures

During the experiment the pigs were observed daily for any abnormalities of general health and behavior by the responsible animal technician or animal caretaker according to standard procedures. All abnormalities (including the presence of any local reactions) were recorded. In case of abnormalities the responsible veterinarian was consulted. Blood samples (serum) were collected just before each vaccination and two weeks after booster vaccination. The samples were transported for blood sampling at ambient temperature. After coagulation the sera were stored frozen until testing in an experimental $rIde_{Ssuis}$ antibody ELISA. Three weeks after booster vaccination, all animals were subjected to a post-mortem examination of the injection sites according to standard procedures.

Laboratory Experimental Procedures

Serology $rIde_{Ssuis}$

The serum samples were tested in an experimental $rIde_{Ssuis}$ ELISA. In short, $rIde_{Ssuis}$ antigen was coated onto microtiter plates. After coating the plates were washed and serial dilutions of sera were made. After incubation and subsequent washing the bound antibodies were quantified using anti-pig IgG conjugate and TMB as substrate. Titres were expressed in $\log_2$. In this test <4.3 is considered negative. For calculation purposes <4.3 is replaced by 3.3.

Serology *E. coli*

The serum samples were tested for K88ab, K88ac, K99, 987P and LT antibody titers. In short, the respective *E. coli* antigens were coated onto microtitre plates. After coating the plates were washed and serial dilutions of sera were made. After incubation and subsequent washing the bound antibodies were quantified by using anti-swine IgG conjugate and TMB as substrate. Titres were expressed in $\log_2$. In this test titres <5.6 are considered negative. For calculation purposes <5.6 is replaced by 4.6.

Serology *C. perfringens*

For *C. perfringens* beta toxin antibody titers were tested in an ELISA method. In short, *C. perfringens* (strain 578) β-toxin was coated onto microtitre plates. After coating and subsequent blocking of the plates, the plates were washed and two-fold serial dilutions of sera were made. After incubation and subsequent washing the bound antibodies were quantified by using anti-ruminant conjugate and TMB as substrate. Titres are expressed in $\log_2$. In this test titres <4.6 are considered negative. For calculation purposes <4.6 is replaced by 3.6.

Serology *P. multocida*

*P. multocida* toxin (PMT) neutralizing antibodies were measured as follows: two-fold serial dilutions of sera were pre-incubated with *P. multocida* type 1 toxin in microtiter plates and then inoculated on a VERO monolayer. The cells were incubated and the inhibition of the cytopathic effect (CPE) of the toxin was measured. Titres are expressed as $\log_2$ of the reciprocal highest dilution where no CPE is observed. In this test a titre <3 is considered negative. For calculation purposes <3 is replaced by 2.

Serology *B. bronchiseptica*

*B. bronchiseptica* agglutinating antibodies were measured in the Blobel test. In short, two-fold serial dilutions of sera were incubated with a *B. bronchiseptica* suspension and agglutination is read. Titres were expressed as the $\log_2$ reciprocal of the highest serum dilution that gave complete agglutination. In this test a titre <1 is considered negative. For calculation purposes <1 is replaced by 0.

Evaluation of Results and Statistical Analysis

The serological results for all vaccine components will be compared between groups i.e. associated mixed use groups will be compared with the respective single vaccine groups. Selected groups were compared using two-sided two-sample t-test and the statistical programme Minitab 17. The test was valid if clear seroconversion was observed in the single vaccine groups post-vaccination.

Results rIdeSsuis Serology

At the start of the study all pigs were seronegative for $rIde_{Ssuis}$ (Table 2). The two associated use groups with Porcilis ColiClos and Porcilis AR-T DF were 3.3 and 2.1 $\log_2$ lower compared to the single vaccines, respectively. These differences were statistically significant: p=0.003 and p=0.020, respectively. The two control groups 4 and 5 remained seronegative during the study.

Porcilis ColiClos Serology: K88ab, K88ac, K99, 987P, LT and Antigens β-Toxin

The addition of rIde$_{S.suis}$ had no negative effect on the serological response against the antigens in Porcilis ColiClos (Table 3-8). A negative trend for 987P response in the associated mixed use group was observed (p=0.061) but the difference in 987P titre was very small (only 1 log$_2$) and probably not biologically relevant.

The respective control groups were seronegative at the start of the study and remained at a low level during the study.

Porcilis AR-T DF Serology: PMT Toxin and *B. bronchiseptica*

At the start of the study the pigs were seronegative for PMT toxin (Table). An apparent statistically significant negative effect of the rIde$_{Ssuis}$ antigen on PMT toxin antibody development was found (p=0.021) and which precludes the combined use of these two vaccine antigens.

After vaccination, no negative effect of the associated mixed use was observed on the *Bordetella* antibody titres.

Local Reactions Injection Site

Necropsy of the vaccine injection sites was done 2 weeks post-vaccination when max/peak reactions are expected, and showed the presence of local reactions after priming (right side) and/or booster (left side) vaccination (not shown). The addition of rIde$_{Ssuis}$ to Porcilis ColiClos or Porcilis AR-T DF did not exacerbate the local reaction compared to those of the single vaccines.

Results of serology tests are shown in the following Tables 2-10. As each group consisted of eight pigs, the antibody titres given in the tables for groups 1 to 5 (groups 1 and 3-5 represent comparative examples) are an average of eight values.

TABLE 2 rIde$_{Ssuis}$ antibody titre

| Group | antibody titre (log$_2$) on post-vaccination day | | |
|---|---|---|---|
| | 0 | 28 | 42 |
| Group 1 rIde$_{Ssuis}$ + Diluvac Forte | 3.3 | 7.8 | 10.1 |
| Group 2 rIde$_{Ssuis}$ + Porcilis ColiClos | 3.8 | 7.4 | 8.7 |
| Group 3 rIde$_{Ssuis}$ + Porcilis AR-T DF | 3.6 | 5.1 | 8.0 |
| Group 4 Porcilis ColiClos | 3.4 | 3.3 | 3.3 |
| Group 5 Porcilis AR-T DF | 3.7 | 3.6 | 3.4 |

TABLE 3

*E. coli* F4ab (=K88ab) antibody titre

| Group | antibody titre (log$_2$) on post-vaccination day | | |
|---|---|---|---|
| | 0 | 28 | 42 |
| Group 1 rIde$_{Ssuis}$ + Diluvac Forte | 4.6 | 4.6 | 4.8 |
| Group 2 rIde$_{Ssuis}$ + Porcilis ColiClos | 4.6 | 6.8 | 9.9 |
| Group 3 rIde$_{Ssuis}$ + Porcilis AR-T DF | 4.6 | 4.6 | 4.6 |
| Group 4 Porcilis ColiClos | 4.6 | 5.7 | 9.1 |
| Group 5 Porcilis AR-T DF | 4.6 | 4.6 | 4.6 |

TABLE 4

*E. coli* F4ac (=K88ac) antibody titre

| Group | antibody titre (log$_2$) on post-vaccination day | | |
|---|---|---|---|
| | 0 | 28 | 42 |
| Group 1 rIde$_{Ssuis}$ + Diluvac Forte | 4.7 | 4.8 | 4.9 |
| Group 2 rIde$_{Ssuis}$ + Porcilis ColiClos | 4.6 | 5.5 | 9.7 |
| Group 3 rIde$_{Ssuis}$ + Porcilis AR-T DF | 4.6 | 5.9 | 4.6 |
| Group 4 Porcilis ColiClos | 4.6 | 5.1 | 9.0 |
| Group 5 Porcilis AR-T DF | 4.6 | 4.6 | 4.6 |

TABLE 5

*E. coli* F5 (=K99) antibody titre

| Group | antibody titre (log$_2$) on post-vaccination day | | |
|---|---|---|---|
| | 0 | 28 | 42 |
| Group 1 rIde$_{Ssuis}$ + Diluvac Forte | 5.5 | 5.6 | 6.3 |
| Group 2 rIde$_{Ssuis}$ + Porcilis ColiClos | 4.6 | 7.3 | 9.8 |
| Group 3 rIde$_{Ssuis}$ + Porcilis AR-T DF | 4.6 | 5.0 | 5.3 |
| Group 4 Porcilis ColiClos | 4.6 | 7.0 | 9.5 |
| Group 5 Porcilis AR-T DF | 4.6 | 5.0 | 5.6 |

TABLE 6

*E. coli* F6 (=987P) antibody titre

| Group | antibody titre (log$_2$) on post-vaccination day | | |
|---|---|---|---|
| | 0 | 28 | 42 |
| Group 1 rIde$_{Ssuis}$ + Diluvac Forte | 6.3 | 8.5 | 9.7 |
| Group 2 rIde$_{Ssuis}$ + Porcilis ColiClos | 5.5 | 10.4 | 14.1 |
| Group 3 rIde$_{Ssuis}$ + Porcilis AR-T DF | 5.0 | 7.1 | 8.6 |
| Group 4 Porcilis ColiClos | 4.8 | 10.8 | 15.3 |
| Group 5 Porcilis AR-T DF | 4.7 | 7.9 | 8.6 |

TABLE 7

*E. coli* LT antibody titre

| Group | antibody titre (log$_2$) on post-vaccination day | | |
|---|---|---|---|
| | 0 | 28 | 42 |
| Group 1 rIde$_{Ssuis}$ + Diluvac Forte | 6.1 | 7.2 | 7.5 |
| Group 2 rIde$_{Ssuis}$ + Porcilis ColiClos | 5.6 | 7.8 | 10.1 |
| Group 3 rIde$_{Ssuis}$ + Porcilis AR-T DF | 5.1 | 5.6 | 6.1 |
| Group 4 Porcilis ColiClos | 4.9 | 7.6 | 9.6 |
| Group 5 Porcilis AR-T DF | 5.2 | 6.0 | 5.9 |

TABLE 8

C. perfringens beta-toxin antibody titre

| Group | antibody titre ($log_2$) on post-vaccination day 0 | 28 | 42 |
|---|---|---|---|
| Group 1 $rIde_{Ssuis}$ + Diluvac Forte | 3.6 | 3.6 | 3.6 |
| Group 2 $rIde_{Ssuis}$ + Porcilis ColiClos | 3.6 | 5.7 | 8.9 |
| Group 3 $rIde_{Ssuis}$ + Porcilis AR-T DF | 3.6 | 3.6 | 3.6 |
| Group 4 Porcilis ColiClos | 3.6 | 6.0 | 8.7 |
| Group 5 Porcilis AR-T DF | 3.6 | 3.6 | 3.8 |

TABLE 9

P. multocida type 1 toxin antibody titre

| Group | antibody titre ($log_2$) on post-vaccination day 0 | 28 | 42 |
|---|---|---|---|
| Group 1 $rIde_{Ssuis}$ + Diluvac Forte | 0.0 | 0.0 | 0.0 |
| Group 2 $rIde_{Ssuis}$ + Porcilis ColiClos | 0.0 | 0.0 | 0.0 |
| Group 3 $rIde_{Ssuis}$ + Porcilis AR-T DF | 0.0 | 0.0 | 1.0 |
| Group 4 Porcilis ColiClos | 0.0 | 0.0 | 0.0 |
| Group 5 Porcilis AR-T DF | 0.0 | 0.0 | 2.8 |

TABLE 10

B. bronchiseptica agglutinating antibody titre

| Group | antibody titre ($log_2$) on post-vaccination day 0 | 28 | 42 |
|---|---|---|---|
| Group 1 $rIde_{Ssuis}$ + Diluvac Forte | 1.8 | 2.3 | 2.1 |
| Group 2 $rIde_{Ssuis}$ + Porcilis ColiClos | 1.6 | 1.0 | 0.8 |
| Group 3 $rIde_{Ssuis}$ + Porcilis AR-T DF | 1.0 | 4.6 | 7.1 |
| Group 4 Porcilis ColiClos | 0.8 | 0.4 | 0.0 |
| Group 5 Porcilis AR-T DF | 1.4 | 5.3 | 8.1 |

Conclusions

As can be seen from the results in Tables 2-10, the addition of $rIde_{S.suis}$ had no negative effect on the serological response of the antigens in Porcilis ColiClos. The addition of $rIde_{Ssuis}$ also had no negative effect on the serological response against the *Bordetella* antigen in Porcilis AR-T DF but did have a significant negative effect on *P. multocida* titre.

In particular, at the first time point of 28 days after vaccination the response against the $rIde_{S.suis}$ antigen is almost at the same level for the combination vaccine with Porcilis ColiClos when compared with the positive control ($rIde_{S.suis}$ only), but substantially lower for the combination vaccine with Porcilis ART-DF (Table 2). Therefore, the Porcilis ColiClos antigens have less negative influence on the response against $rIde_{S.suis}$ than the Porcilis ART antigens. In addition, at the second time point of 42 days after vaccination the response against *P. multocida* is substantially lower for the combination of $rIde_{S.suis}$ and Porcilis AR-T DF compared to Porcilis AR-T DF (Table 9). Hence, the presence of $rIde_{S.suis}$ in the combination vaccine has a significant negative influence on the response against *P. multocida*.

These findings show that the combination of the $rIde_{S.suis}$ antigen with the *P. multocida* and *B. bronchisepta* antigens and toxoids included in Porcilis AR-T DF is not feasible, whereas the combination of $rIde_{S.suis}$ with *E. coli* and *Clostridium* antigens and toxoids included in Porcilis Coli-Clos results in excellent results, making this combination particular suitable for the provision of a combination vaccine. Inherently, the same can be concluded for a combination vaccine comprising less antigens, for example only the fimbrial antigens of *Escherícha coli* which are the essential antigens to provide adequate protection against *E. coli.*

From the results in can thus be concluded that the combination of $rIde_{S.suis}$ with *E. coli* and *Clostridium* antigens and toxoids is suitable for use in a combination vaccine for providing protection against pathogenic infections caused by *S. suis, E. coli* and *Clostridium*. Thus, it has surprisingly become possible in the present invention to provide a vaccine, which provides protection against a combination of diseases including pathogenic infections caused by *S. suis, E. coli* and *Clostridium* and which is suitable for sow vaccination. Also, given the fact that it was shown that offspring could be adequately protected against an infection with *Streptococcus suis* via the intake of colostrum (for the other antigens this effect is known form the prior art), it is believed that the combination vaccine, providing high titers in the vaccinated female animals, is able to provide adequate protection against all three pathogens via the intake of colostrum.

The invention claimed is:

1. A vaccine comprising components (a), (b) and (c) of:

(a) an immunologically effective amount of a *Streptococcus suis* IgM protease antigen, (b) an immunologically effective amount of an *Escherichia coli* fimbrial antigen, and (c) an immunologically effective amount of a *Clostridium* toxoid.

2. The vaccine according to claim 1, characterized in that component (b) comprises one or more *Escherichia coli* fimbrial antigens selected from F4, F5, F6, F18, and F41.

3. The vaccine according to claim 2, characterized in that component (b) comprises at least the fimbrial *Escherichia coli* antigens F4, F5 and F6.

4. The vaccine according to claim 1, characterized in that component (b) further comprises an *Escherichia coli* toxoid.

5. The vaccine according to claim 4, characterized in that the *Escherichia coli* toxoid is *Escherichia coli* LT toxoid.

6. The vaccine according to claim 1, characterized in that component (c) comprises *Clostridium perfringens* Type C toxoid.

7. The vaccine according to claim 6, characterized in that component (c) further comprises *Clostridium perfringens* Type B toxoid.

8. The vaccine according to claim 1, characterized in that component (b) comprises the *Escherichia coli* fimbrial antigens F4, F5, and F6 and component (c) comprises the *Clostridium perfringens* type C toxoid.

9. The vaccine according to claim 1, characterized in that the vaccine comprises an adjuvant.

10. The vaccine according to claim 1, characterized in that the vaccine is adapted for intramuscular injection.

11. A method for protecting a pig against *Streptococcus suis, Escherichia coli* and *Clostridium* comprising administering the vaccine of claim 1 to the pig.

12. A method for protecting a piglet against a pathogenic infection with *Streptococcus suis, Escherichia coli* and *Clostridium*, comprising administering the vaccine of claim 1 to a female pig in order to protect the piglet against a pathogenic infection with *Streptococcus suis* through the intake by the piglet of colostrum from the female pig following said administering of the vaccine to the female pig.

13. A kit of parts comprising multiple separate vaccine containers, one of which comprises an immunologically effective amount of a *Streptococcus suis* IgM protease antigen, and one or more additional containers in combination comprise an immunologically effective amount of an *Escherichia coli* fimbrial antigen, and an immunologically effective amount of a *Clostridium* toxoid.

14. A method for protecting an animal against *Streptococcus suis* infection, *Escherichia coli* infection and *Clostridium* infection, comprising administering a vaccine comprising an immunologically effective amount of a *Streptococcus suis* IgM protease antigen;
    wherein the IgM protease antigen is mixed with an immunologically effective amount of an *Escherichia coli* fimbrial antigen, and an immunologically effective amount of a *Clostridium* toxoid, before administration of the vaccine.

\* \* \* \* \*